(12) United States Patent
Kunik et al.

(10) Patent No.: US 8,324,443 B2
(45) Date of Patent: Dec. 4, 2012

(54) SECURE CONTAINERS HAVING UNIDIRECTIONAL APPARATUSES FOR USED OR UNUSED MATERIALS AND METHODS FOR MAKING AND USING SAME

(75) Inventors: Burton J. Kunik, Houston, TX (US); James C. Berns, Carthage, TX (US); Al Aladwani, Missouri City, TX (US); Claude Dance, Dripping Spring, TX (US); David G. Gossman, Zwingle, IA (US)

(73) Assignee: Sharps Compliance, Inc., Houston, TX (US)

( * ) Notice: Subject to any disclaimer, the term of this patent is extended or adjusted under 35 U.S.C. 154(b) by 233 days.

(21) Appl. No.: 12/814,251

(22) Filed: Jun. 11, 2010

(65) Prior Publication Data

US 2011/0303666 A1 Dec. 15, 2011

(51) Int. Cl.
*C21B 3/06* (2006.01)
(52) U.S. Cl. .......... 588/251; 588/249; 588/405
(58) Field of Classification Search .......... 588/249, 588/251, 405; 206/363
See application file for complete search history.

(56) References Cited

U.S. PATENT DOCUMENTS

| | | |
|---|---|---|
| 4,121,755 A | 10/1978 | Meseke et al. |
| 4,315,592 A | 2/1982 | Smith |
| 4,452,358 A | 6/1984 | Simpson |
| 4,494,652 A | 1/1985 | Nelson et al. |
| 4,534,489 A | 8/1985 | Bartlett |
| 4,576,281 A | 3/1986 | Kirksey |
| 4,662,516 A | 5/1987 | Baker, Sr. et al. |
| 4,842,138 A | 6/1989 | Sandel et al. |
| 4,846,397 A | 7/1989 | Copeland |
| 4,863,052 A | 9/1989 | Lambert |
| 4,886,164 A | 12/1989 | Stein et al. |
| 4,969,596 A | 11/1990 | Schulbaum |
| 4,978,028 A | 12/1990 | George et al. |
| 5,039,004 A | 8/1991 | Simpson |
| 5,046,614 A | 9/1991 | Torres et al. |
| 5,080,251 A | 1/1992 | Noack |
| 5,240,176 A | 8/1993 | Akers |
| 5,291,997 A | 3/1994 | He et al. |
| 5,356,022 A | 10/1994 | Tipps |
| 5,385,105 A | 1/1995 | Withers, Jr. et al. |
| 5,395,008 A | 3/1995 | Bemis et al. |
| 5,427,238 A | 6/1995 | Weiss |
| 5,511,657 A | 4/1996 | Gnau, III et al. |
| 5,570,783 A | 11/1996 | Thome et al. |
| 5,615,795 A | 4/1997 | Tipps |
| 5,630,506 A | 5/1997 | Thorne et al. |
| 5,687,839 A | 11/1997 | Gnau, III et al. |
| 5,992,634 A | 11/1999 | Woodring et al. |
| 6,019,242 A | 2/2000 | Wysocki et al. |
| 6,283,909 B1 | 9/2001 | Sharp |
| 6,742,703 B2 | 6/2004 | Esakov et al. |

*Primary Examiner* — Edward Johnson
(74) *Attorney, Agent, or Firm* — Robert W Strozier

(57) ABSTRACT

Secure containers are disclosed for disposal of unused, experimental, and/or expired pharmaceuticals, nutraceuticals, veterinary medicines, and/or similar materials, where the containers include at least one unidirectional apparatus for depositing materials into an interior of the container, while resisting normal attempts at retrieval of deposited materials. Methods are also disclosed for making and using the secure containers including a unidirectional member supporting deposition of materials into an interior of the container, while resisting withdrawal of deposited materials.

18 Claims, 18 Drawing Sheets

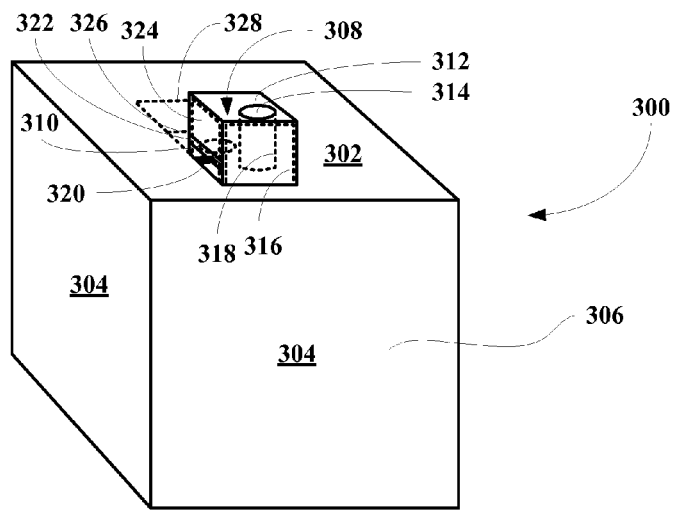
FIG. 3A
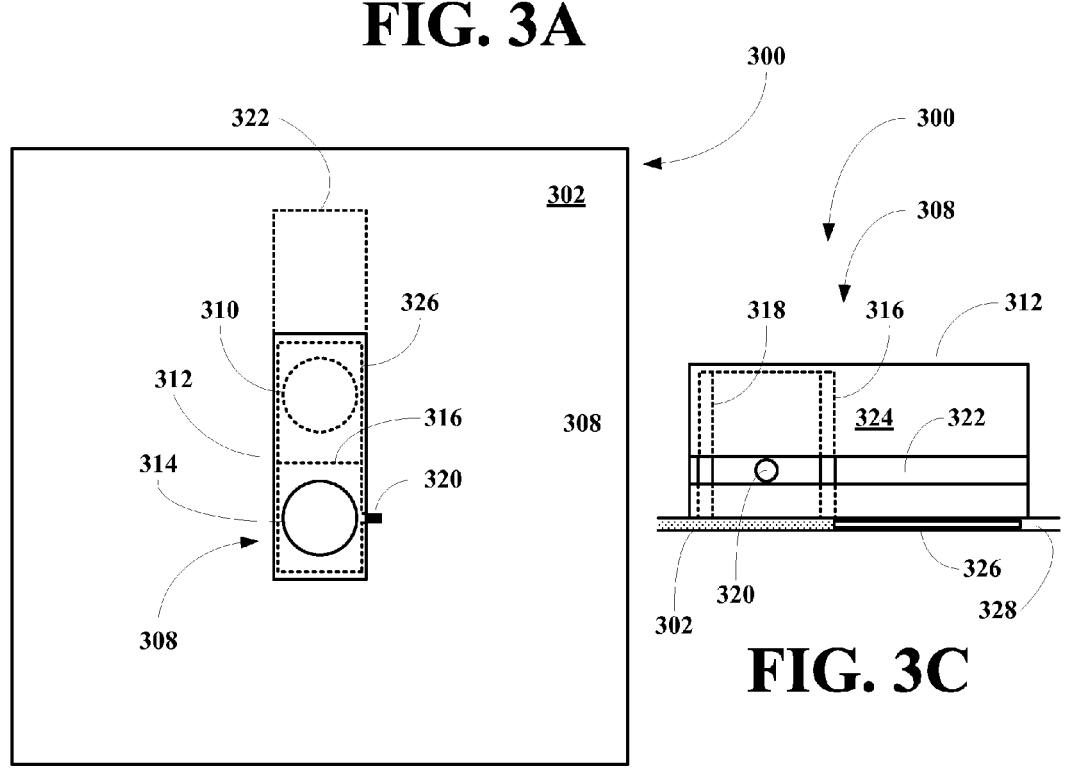
FIG. 3B
FIG. 3C

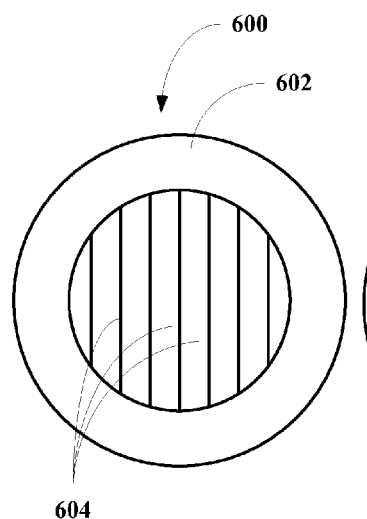 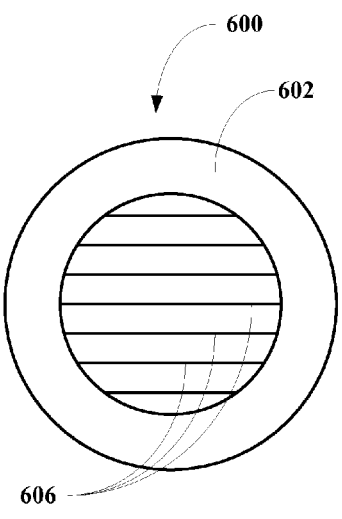 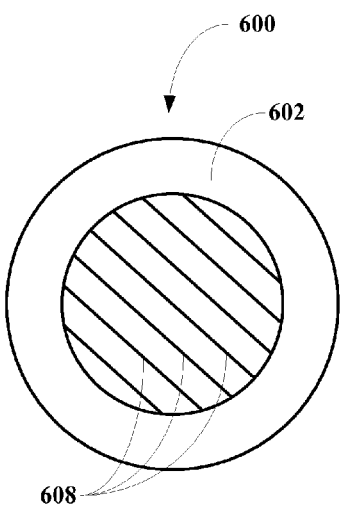
FIG. 6A     FIG. 6B     FIG. 6C
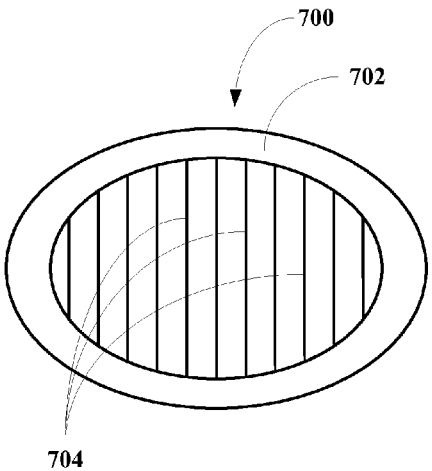 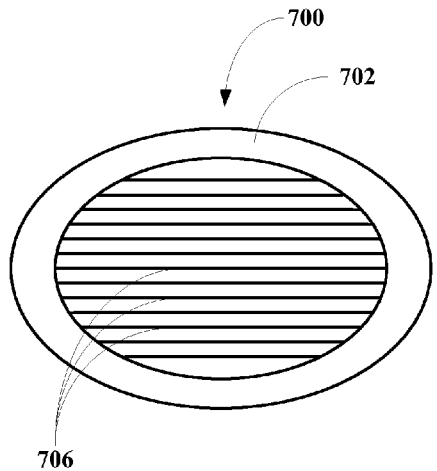
FIG. 7A     FIG. 7B

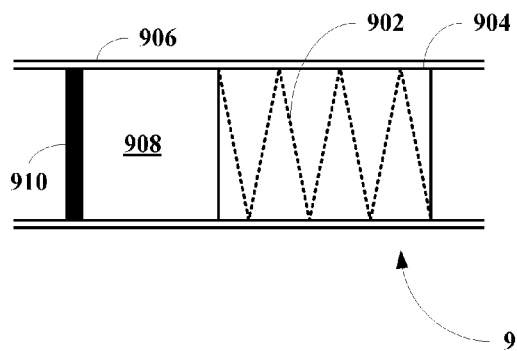
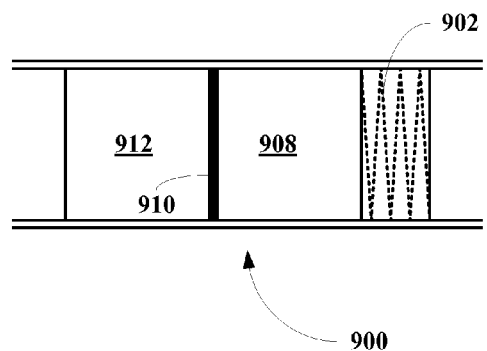
FIG. 9A  FIG. 9B
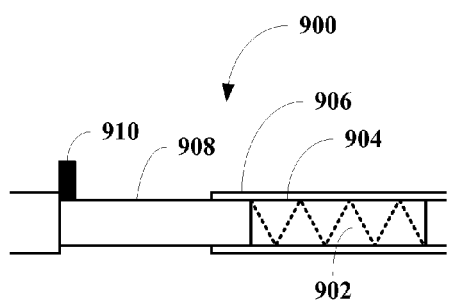
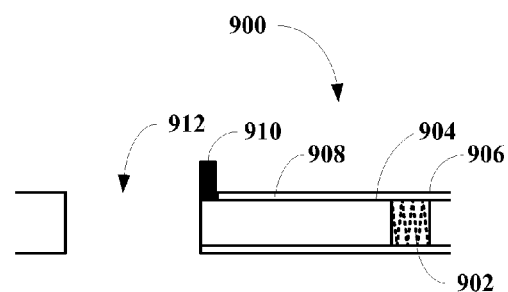
FIG. 9C  FIG. 9D

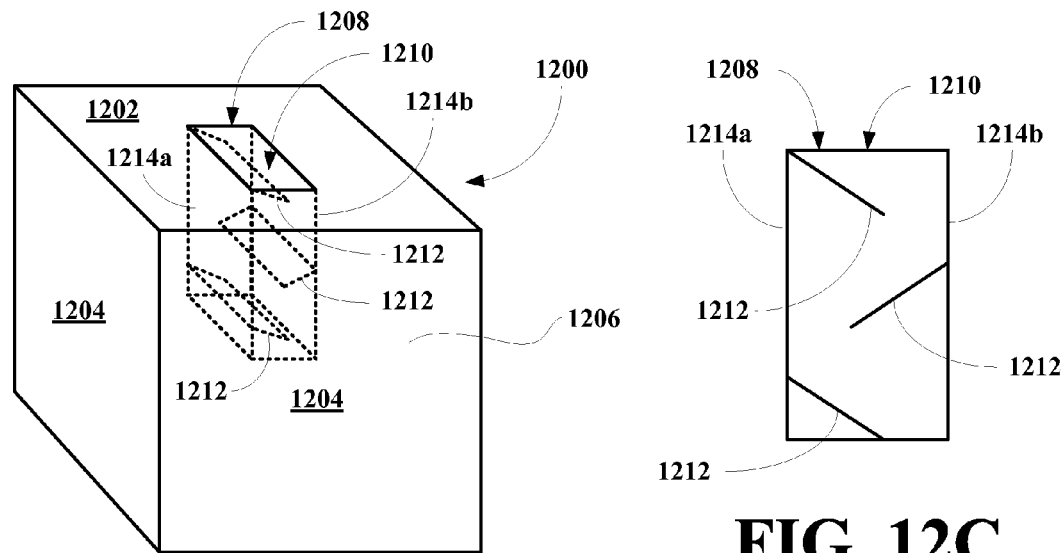
FIG. 12A
FIG. 12C
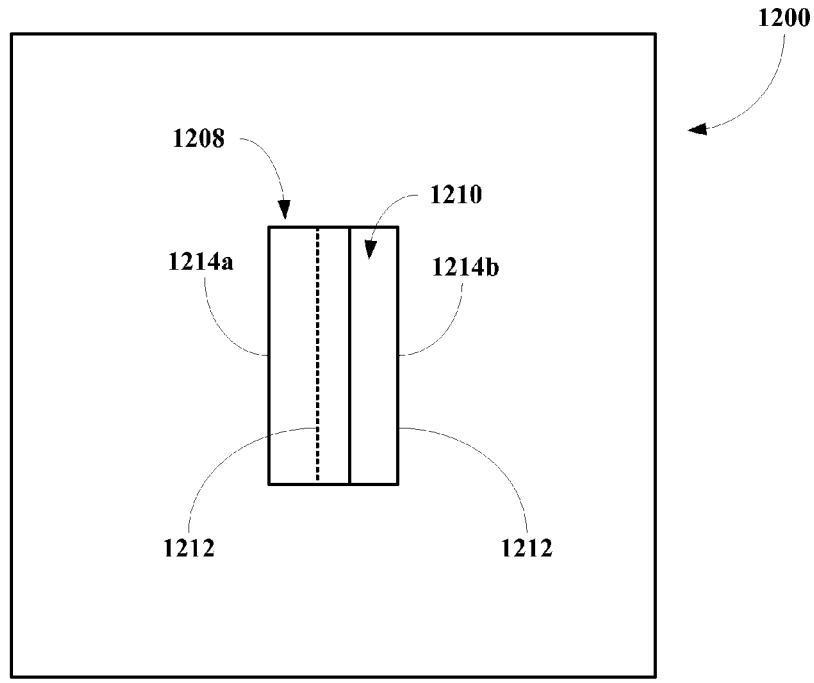
FIG. 12B

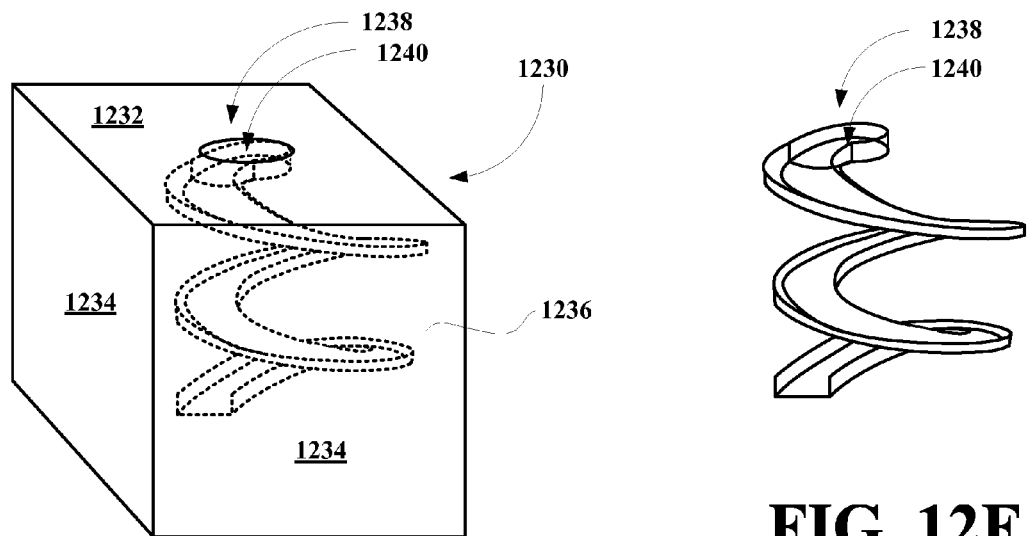
FIG. 12D
FIG. 12F
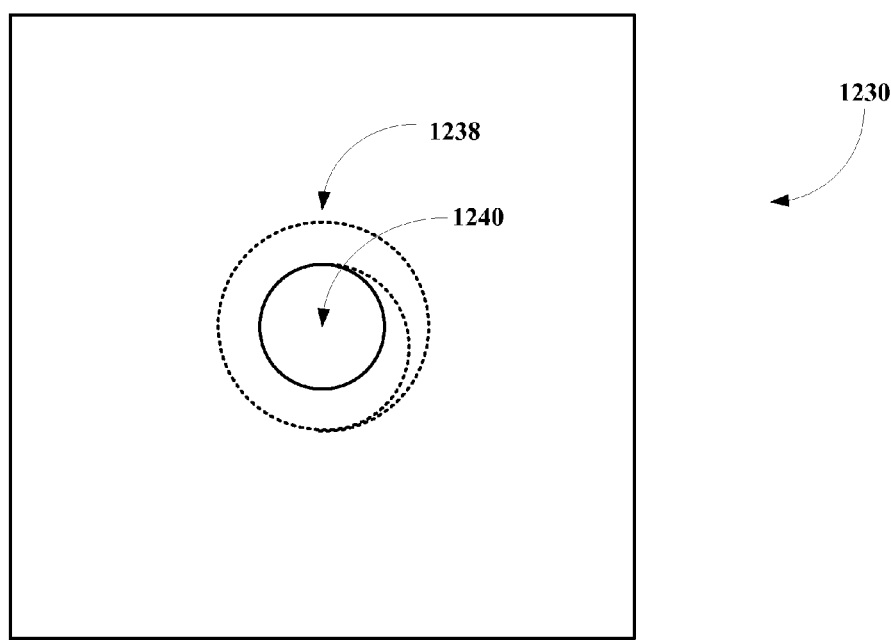
FIG. 12E

SECURE CONTAINERS HAVING UNIDIRECTIONAL APPARATUSES FOR USED OR UNUSED MATERIALS AND METHODS FOR MAKING AND USING SAME

RELATED APPLICATIONS

The present invention is related to co-pending U.S. patent application Ser. Nos. 12/610,331, filed Nov. 1, 2009; 12/649,215 filed Dec. 29, 2009; 12/649,230 filed Dec. 29, 2009; and 12/713,733 filed Feb. 26, 2009, incorporated by reference through the operation of the closing paragraph of the specification.

BACKGROUND OF THE INVENTION

1. Field of the Invention

Embodiments of the present invention relate to secure containers for disposal of used and/or unused source materials, especially pharmaceuticals, nutraceuticals, and/or veterinary medicines and to methods for making and using the containers.

More particularly, embodiments of the present invention relate to secure containers for disposal of used and/or unused source materials, especially pharmaceuticals, nutraceuticals, and/or veterinary medicines, where the containers include at least one unidirectional apparatus for depositing source materials into an interior of the container, where the apparatuses are adapted to permit deposition of source materials therein, while resisting normal attempts of retrieval of source materials deposited therein. The present invention also relates to methods for making and using the secure container, where the containers include an interior and a top, where the top includes at least one opening including a unidirectional apparatus supporting deposition of source materials into an interior of the container, while resisting retrieval of deposited materials.

2. Description of the Related Art

Disposal of unused, expired and/or experimental pharmaceuticals, nutraceuticals, veterinary medicines, bio-medical materials and/or other materials produced by the pharmaceutical, nutraceutical, veterinary, bio-technology, medical or other industries is a growing problem. Many of these pharmaceuticals, nutraceuticals, veterinary medicines, and/or other materials may be harmful, especially to children or may be used for nefarious purposes. Currently, many pharmaceuticals, nutraceuticals, veterinary medicines, and/or similar materials are simply flushed down toilets, but this causes certain environmental problems.

Currently, there is no efficient and cost-effective way to collect and dispose of pharmaceuticals, nutraceuticals, veterinary medicines, and/or similar materials. This problem is specially acute in homes and in small facilities, where pickup disposal services may be inconvenient and expensive.

Thus, there is a need in the art for secure containers for collection, transportation and disposal of pharmaceuticals, nutraceuticals, veterinary medicines, and/or similar materials.

SUMMARY OF THE INVENTION

Embodiments of the present invention provide secure containers for disposal of used, unused, experimental, and/or expired source materials, especially pharmaceuticals, nutraceuticals, veterinary medicines, and/or other materials produced by the pharmaceutical, nutraceutical, veterinary, bio-technology or medical industries, where the containers include a closed interior accessible only through at least one opening, where each opening includes a unidirectional apparatus, which permits insertion of source materials therein, while resisting normal attempts at withdrawal of the source materials deposited therein.

Embodiments of the present invention provide methods for placing used, unused, experimental, and/or expired source materials, especially pharmaceuticals, nutraceuticals, veterinary medicines, and/or other materials produced by the pharmaceutical, nutraceutical, veterinary, bio-technology or medical industries. In certain embodiments, the containers may be positioned in locations where source materials are generated. The methods also include depositing used, unused, experimental, and/or expired source materials into an interior of a container through the at least one opening, where each opening includes a unidirectional apparatus permitting insertion of materials therein, while resisting normal attempts at withdrawal of the materials deposited therein. The methods also include sealing the container and/or the openings to form a sealed container. The methods also include transporting the sealed containers via a delivery service to a processing facility for processing and/or disposing of the sealed containers.

BRIEF DESCRIPTION OF THE DRAWINGS

The invention may be better understood with reference to the following detailed description together with the appended illustrative drawings in which like elements are numbered the same:

FIGS. 3A-C depict an embodiment of a secure box type container of this invention including a third type of unidirectional apparatuses of this invention.

FIGS. 6A-C depict an embodiments of the second type of unidirectional apparatuses of this invention.

FIGS. 7A&B depict an embodiment of the second type of unidirectional apparatuses of this invention.

FIGS. 9A-D depicts an embodiment of a sixth type of unidirectional apparatuses of this invention.

FIG. 12A-C, depict an embodiment of a seventh type of unidirectional apparatuses of this invention.

FIG. 12D-F, depict another embodiment of a seventh type of unidirectional apparatuses of this invention.

DETAILED DESCRIPTION OF THE INVENTION

Figure 1A:
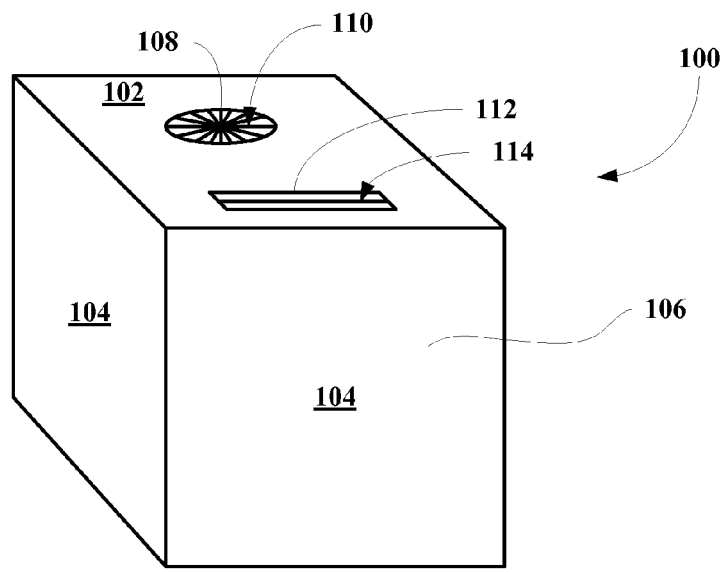
FIGS. 1A&B depict an embodiment of a secure box type container of this invention including a circular opening having an embodiment of a first type of unidirectional apparatuses and rectangular opening having embodiment of a second type of unidirectional apparatuses.
Figure 1B:
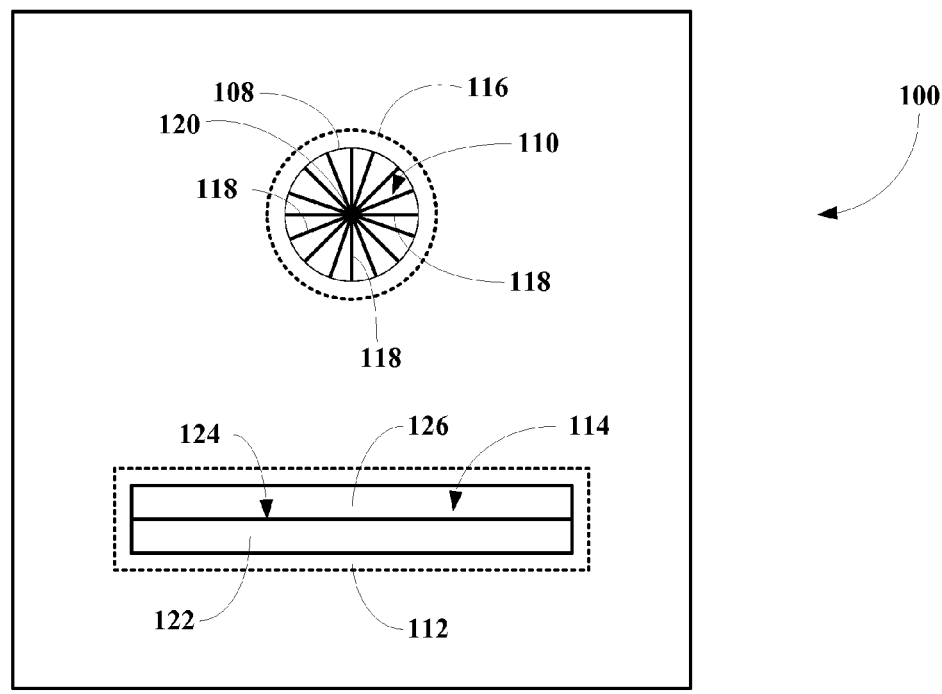
FIG. 1C depict the container of FIGS. 1A&B including a closing member and sealing members of this invention.
FIGS. 1D-G, depicts embodiments of the second type of unidirectional apparatuses having different slit configurations of this invention.

The inventors have found that secure containers can be constructed for disposal of used, unused, experimental, and/or expired source materials, especially pharmaceuticals, nutraceuticals, veterinary medicines, and/or similar materials, where the containers include an interior and at least one unidirectional apparatus for depositing materials into the interior of the container, while resisting normal attempts at withdrawal of deposited materials from the interior thereof. The term "normal attempts at withdrawal" means trying to insert a hand or fingers into the container through the unidirectional apparatuses, where such insert could result in injury. The term "normal attempts at withdrawal" does not include cutting the containers, tearing the containers, or other processes that destroy all or a part of the containers.

Embodiments of the present invention broadly relate to secure containers for disposal of unused, experimental, and/or expired pharmaceuticals, nutraceuticals, veterinary medicines, and/or similar materials, where the containers includes a closed interior accessible only through at least one opening, where each opening includes a unidirectional apparatus permitting insertion of unused, experimental, and/or expired pharmaceuticals, nutraceuticals, veterinary medicines, and/or similar materials into an interior of the containers, while resisting normal attempts at withdrawal of the unused, experimental, and/or expired pharmaceuticals, nutraceuticals, veterinary medicines, and/or similar materials from the interior once deposited therein.

Embodiments of the present invention broadly relate to methods for disposing of unused, experimental, and/or expired pharmaceuticals, nutraceuticals, veterinary medicines, and/or similar materials, where the methods include positioning a secure container of this invention in a location where unused, experimental, and/or expired pharmaceuticals, nutraceuticals, veterinary medicines, and/or similar materials are collected for processing and/or disposal. The methods also include placing unused, experimental, and/or expired pharmaceuticals, nutraceuticals, veterinary medicines, and/or similar materials into an interior of a container through at least one opening having a unidirectional apparatus permitting insertion of materials, while resisting normal attempts at withdrawal of materials deposited therein. The methods also include sealing a filled container and/or sealing the opening of a filled container to form a sealed container. The methods also include transporting the sealed container via a delivery service to a processing facility. The methods optionally include post-processing the sealed container, where the post-processing may include processes to alter or change specific combustion properties of the filled containers or to impart designed barrier properties (e.g., gas resistance, water resistance, solvent resistance, hardening, and/or other barrier properties to the filled container). The methods can also include burning the sealed containers and/or the post-processed sealed container in a combustion facility, where either a portion of generated heat from combustion of the containers is converted into a useable form of energy or a portion of the generated heat and the ash is used to form a useable product.

Embodiments of the present invention broadly relate to systems including a source of secure containers of this invention, a distribution subsystem for delivering secure containers to locations where source materials are generate so that the source materials are collected in the containers through an opening in the container to produce filled containers and sealed for pickup, and a collection subsystem for picking up sealed and filled containers and delivering the sealed and filled containers to a processing facility. The systems may also include a post-processing subsystem for pos-processing the sealed and filled containers to alter or change specific combustion properties of the containers or to impart designed barrier properties to the containers, where the barrier property includes gas resistance, water resistance, solvent resistance, hardening, and/or other barrier properties to the filled container. The system may also include a combustion subsystem for burning the sealed and filled containers and/or the post-processed sealed containers, where either a portion of generated heat from combustion of the containers is converted into a useable form of energy or a portion of the generated heat and the ash is used to form a useable product.

The containers of the present invention can be of any desired size and shape including at least one opening having a unidirectional apparatus, which permits materials to be deposited into the interior of the container, while resisting normal attempts at withdrawal of materials disposed therein.

Suitable Structures Used in the Invention

Suitable container shapes include, without limitation, a polygonal solid such as a rectangular solid, such as a box; a cylinder such as a barrel; a sphere; an ellipsoidal solid; a trapezoidal solid; any other geometrically shaped container or mixtures or combinations thereof.

Suitable opening shapes include, without limitation, circular, ellipsoidal, polygonal such as a triangular opening, a square opening, rectangular opening, a hexagonal opening, etc., any other opening shape, and/or mixtures or combinations thereof.

Suitable unidirectional apparatus include, without limitation, any structure that permits deposing into an interior of a container, while resisting normal attempts at withdrawal of materials deposited therein. Without limiting the structures of the unidirectional apparatus suitable for use in this invention, a set of structures are set forth below referred to herein is first type, second type, third type, fourth type, fifth type, sixth type and seventh type unidirectional apparatus designed to permit deposition into an interior of a container, while resisting normal attempts at withdrawal of materials deposited therein. A container may include one unidirectional apparatus or combination of unidirectional apparatuses.

A first type of unidirectional apparatuses include having a plurality of radial slits, where the member can be any regular or irregular shape and the radial slits extend from a center of the member outward to a boundary for affixing the member into the top of the container. The first type of unidirectional apparatuses are sometimes referred to as radially slitted unidirectional apparatuses. In certain embodiment, the member is flat or substantially flat (less than about 5% deflection from flat).

A second type of unidirectional apparatus includes a flat or substantially flat member (less than about 5% deflection from flat) having one longitudinal, lateral, or slanted slit or a plurality of such slits, where the member can be any regular or irregular shape, and the slits extend between a boundary for affixing the member into the top of the container. The second type of unidirectional apparatuses are sometimes referred to as non-radially slitted unidirectional apparatuses. When a member includes a plurality of slits, the slits may be arranged in a pattern.

A third type of unidirectional apparatus includes a housing having an opening in its top and a slidable member disposed in an interior of the housing. The slidable member includes a hollow cavity within which material can be placed. The slidable member is slidable within the housing by a handle attached to the slidable member and movable within a longitudinal slot in the housing. Once material is placed within the hollow cavity, the slidable member is moved so that the hollow member aligned with an opening in the top of the container such that the material falls into an interior of the container. This type of unidirectional apparatus restricts normal attempts to withdraw deposited materials. The third type of unidirectional apparatuses are sometimes referred to as slidable unidirectional apparatuses.

A fourth type of unidirectional apparatus includes a rotatable member having an opened interior. Material is placed in the interior of the rotatable member. The rotatable member is rotated 180° resulting in the material in the interior being deposited in the interior of the container. This type of unidirectional apparatus restrict normal attempts to withdraw deposited materials. The fourth type of unidirectional apparatuses are sometimes referred to as rotatable unidirectional apparatuses.

A fifth type of unidirectional apparatus includes a flat or substantially flat member (less than about 5% deflection from flat) having one or a plurality of arcuate slits and tabs, where the arcuate slits form portions of member that can rotate about tabs allowing material to pass into the interior of the container, while resisting normal attempts of withdrawal of deposited material. The fifth type of unidirectional apparatuses are sometimes referred to as arcuate slitted unidirectional apparatuses.

A sixth type of unidirectional apparatus includes at least one biased slidable member including a handle mounted in an opening in the top of the container. When the slidable member is moved to open the opening, the biased member is compressed. Once material is placed into the container through the opening, the slidable member is released and the biased member quickly restores the slidable member to its closed state. This type of apparatus permits material deposition, while resisting normal attempts of withdrawal of deposited material. The sixth type of unidirectional apparatuses are sometimes referred to as biased unidirectional apparatuses.

A seventh type of unidirectional apparatus includes a chute including baffles mounted in an opening in the top of the container. The seventh type of unidirectional apparatus also includes a chute having a spiraled configuration. The seventh type of unidirectional apparatus also includes a chute having a zig-zag configuration. The seventh type of unidirectional apparatus also includes a chute having any other configuration that resists normal attempts at withdrawal of deposited materials from the interior of the container.

For unidirectional apparatus that include a flat member, suitable flat member can be, without limitation, rigid members, semi-rigid members, flexible members, resilient members, and/or mixture or combinations thereof. In certain embodiments, the members are constructed out of corrugated plastic materials.

Suitable Reagents Used in the Invention

Suitable materials used in the construction of the containers of this invention include, without limitation, pulp materials, polymer materials, fibrous materials, fabric material, metallic materials, ceramic materials, composite materials, and/or mixtures or combinations thereof. The containers can also be coated with a coating material before and/or after being filled. The construction materials can also be coated with a coating material before and/or during construction.

Pulp materials suitable for use herein include, without limitation, wood, wood chips, sawdust, paper, cardboard, and/or mixtures or combinations thereof.

Fiber materials suitable for use herein include, without limitation, natural fibers, synthetic fibers, or other fibrous material and/or mixtures or combinations thereof. Exemplary fibers include, without limitation, inorganic fibers, carbon fibers, boron-nitride fibers, organic fibers, ceramic fibers, glass fibers, any other fibrous material and mixtures or combinations thereof.

Fabric materials suitable for use herein include, without limitation, any natural or synthetic fabric and/or mixtures or combinations thereof. Exemplary fabric materials include, without limitation, cotton, wool and other fabrics made from animals or plants, RAYON, DACRON, fabric made of polyamides, or any other fabric and/or mixtures or combinations thereof.

The metal or metallic materials include, without limitation, any metal or metal alloy including a metal from the periodic table of elements. Exemplary metals or metallic materials include, alkali metals (Group 1 metals), alkaline earth metals (Group 2 metals), transition metals (Group 3-12 metals), Lanthanide metals, Actinide metals, post-transition metals, metalloids, and/or mixtures or combinations thereof. Certain metals and metalloids may be removed prior to use. The metals may be in any form, including powders, flakes, fibers, wires, pieces, devices including metals, or other metal containing object or devices, and/or mixtures or combinations thereof. Exemplary devices include waste electronic devices. It should be recognized by one of ordinary skill in the art, that certain metals and metal alloys either pose a health or environmental concerns or issues or produce concerns or issues once combusted. Examples of such metals or metal alloys include mercury, cadmium, lead, and thallium and radioactive elements and/or isotopes.

Ceramic materials suitable for use herein include, without limitation, any ceramic material or ceramic-containing material and/or mixtures or combinations thereof. Exemplary ceramic materials include, without limitation, electronic substrates, glass, dishes, clay pots, any other object that contains a ceramic material, and/or mixtures or combinations thereof.

Exemplary polymer materials suitable for use herein include, without limitation, plastics, thermoplastics, elastomers, thermoplastic elastomers, thermosetting resins, other polymers or polymeric materials and/or mixtures or combinations thereof.

Suitable coating materials include, without limitation, oils (synthetic oils or natural animal or plant oils), medium to high melting point hydrocarbons, waxes, oligomers, low molecular weight polymers, high molecular weight polymers, resins, thermosetting resins, thermoplastics, elastomers, photocurable monomers, thermally curable monomers, curable monomers, polymerizable monomers, photocurable oligomers, thermally curable oligomers, polymerizable oligomers, photocurable polymers, thermally curable polymers, polymerizable polymers, other materials that can form a desired coating or particle coating on the particulate fuels of this invention or mixture or combinations thereof. The coatings are designed to augment, adjust, change or alter one or more characteristics of the container.

Suitable Reagents and Equipment of the Invention

Suitable materials for construction of the containers include, without limitation, plastics, rubbers, metals, woods, ceramics, composites, or mixtures or combinations thereof.

DETAILED DESCRIPTION OF THE DRAWINGS

Referring now to FIGS. 1A&B, an embodiment of a secure box type container of this invention, generally 100, is shown to include a top 102, five side 104 (two of which are shown here) and an interior 106. The top 102 includes a circular opening 108 having an embodiment of a first type of a unidirectional apparatus 110 and a rectangular opening 112 having an embodiment of a second type of a unidirectional apparatus 114. The first type of a unidirectional apparatus 110 includes a circular member 116 having a plurality of radial slits 118. The radial slits 118 allow items to be inserted into the interior 106. The radial slits 118 and the resiliency of the material comprising the member 116 resist a user placing a hand or portion thereof into the opening 108 through the apparatus 110 and then attempting to remove material inside without suffering pricks from tips 120 formed by the radial slits 118. The second type of a unidirectional apparatus 114 includes a rectangular member 122 including a longitudinal slit 124. The longitudinal slit 124 and the resiliency of the material comprising the member 122 resist a user placing a hand or portion thereof into the opening 112 through the apparatus 114 and then attempting to remove material inside without suffering contact with edges 126 formed by the longitudinal slit 124.

Figure 1C:
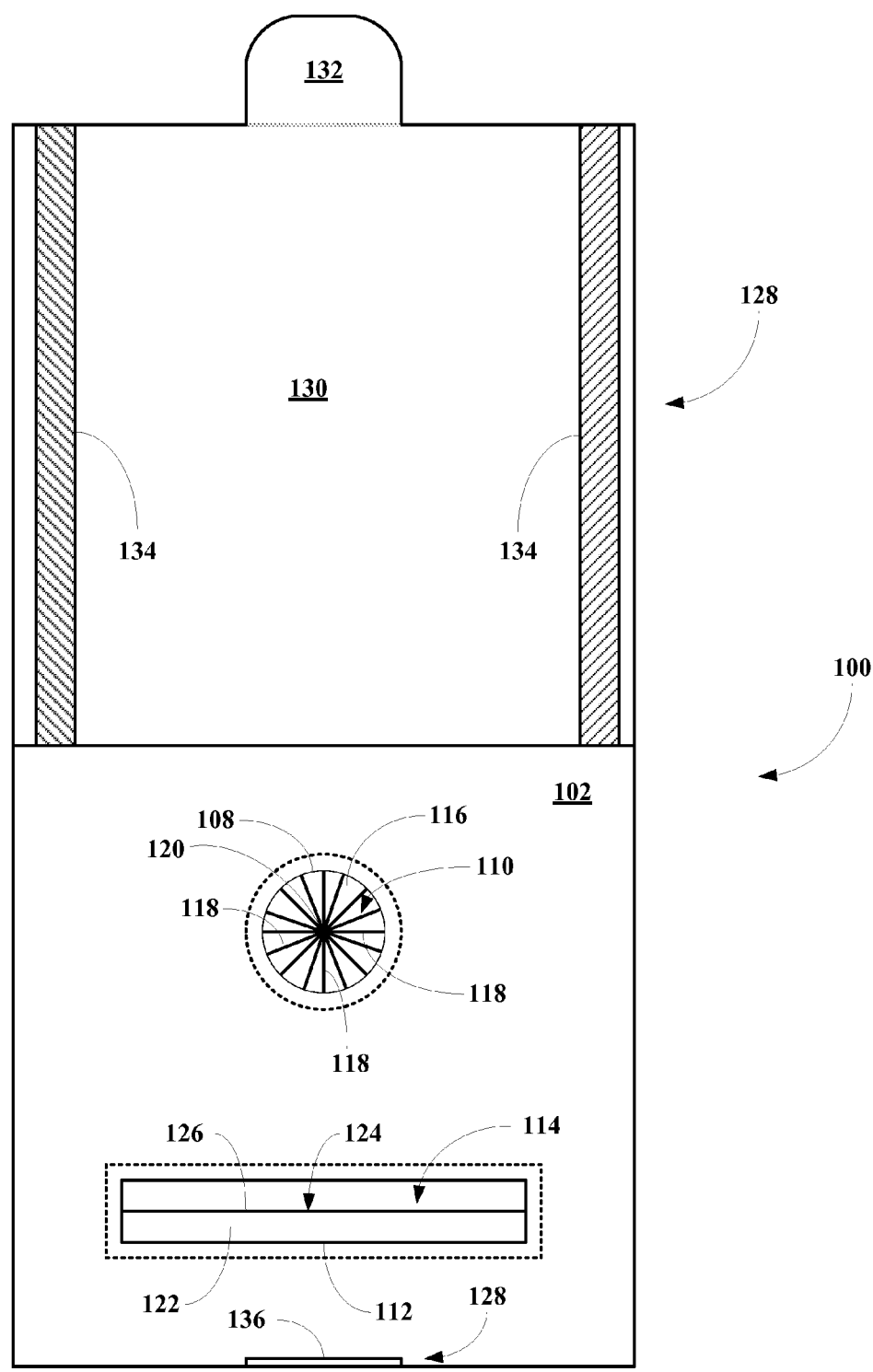

Referring now to FIG. 1C, an embodiment of the container 100 of FIG. 1A&B is shown to also include a closing/sealing assembly 128. The closing member/sealing assembly 128 includes a closing member 130 having the same or substantially the same shape as the top 102, where substantially the same means that the closing member covers at least 90% of the surface area of the top 102. The assembly 128 also includes an insertion tab 132 and two adhesive strips 134 covered with at release sheet (not shown). In this embodiments, the top 102 includes a rectangular tab insertion slot 136 into which the insertion tab 132 is inserted when the closing member 130 is in its closed state. The container 100 may be opened and closed during fillings without sealing the closing member 130 in place. However, once the release sheets over the adhesives strips 134 have been removed, when the closing member 130 engages the top 102 and the insertion tab 132 is inserted into the slot 136, the container 100 is sealed for transport to a processing facility.

Figure 1D:
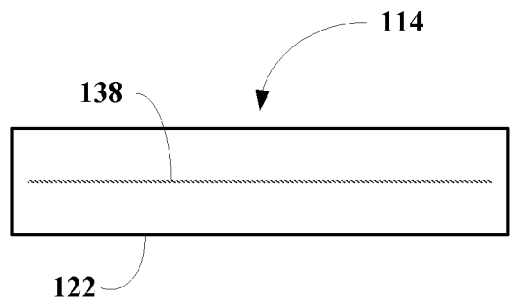
Figure 1E:
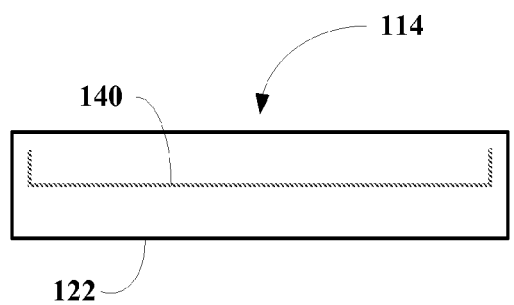
Figure 1F:
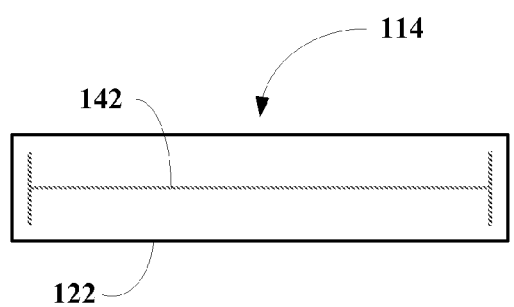
Figure 1G:
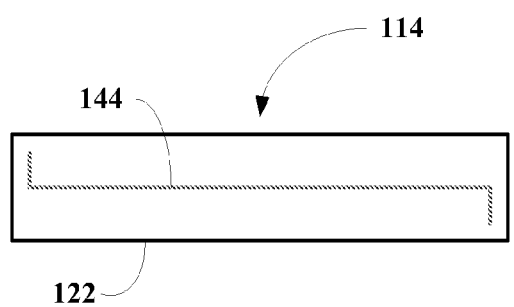

Referring now to FIG. 1D, the apparatus 114 is shown to include the rectangular member 112 having a longitudinal slit 138. Referring now to FIG. 1E, the apparatus 114 is shown to include the rectangular member 122 having a U-shaped longitudinal slit 140. Referring now to FIG. 1F, the apparatus 114 is shown the rectangular member 122 having a I-beam-shaped longitudinal slit 142. Referring now to FIG. 1G, the apparatus 114 is shown the rectangular member 122 having a Z-shaped longitudinal slit 144. Of course, the corners do not have to be right angles, the corners may have angles other than right angle or rounded.

Figure 2A:
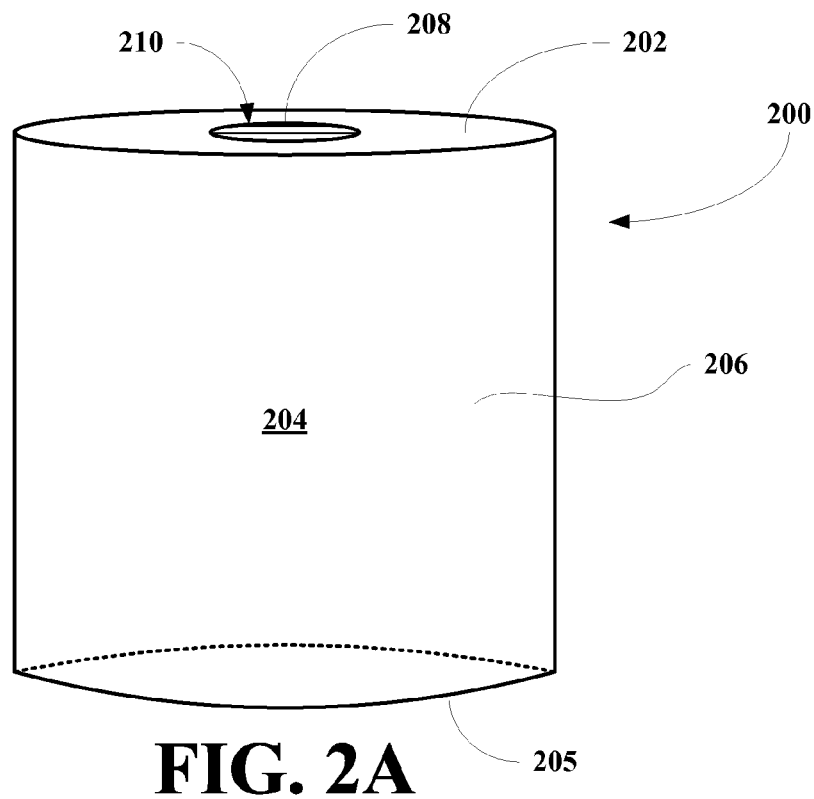
FIGS. 2A&B depict an embodiment of a secure barrel type container of this invention including a circular opening having an embodiment of a second type of unidirectional apparatuses of this invention.
Figure 2B:
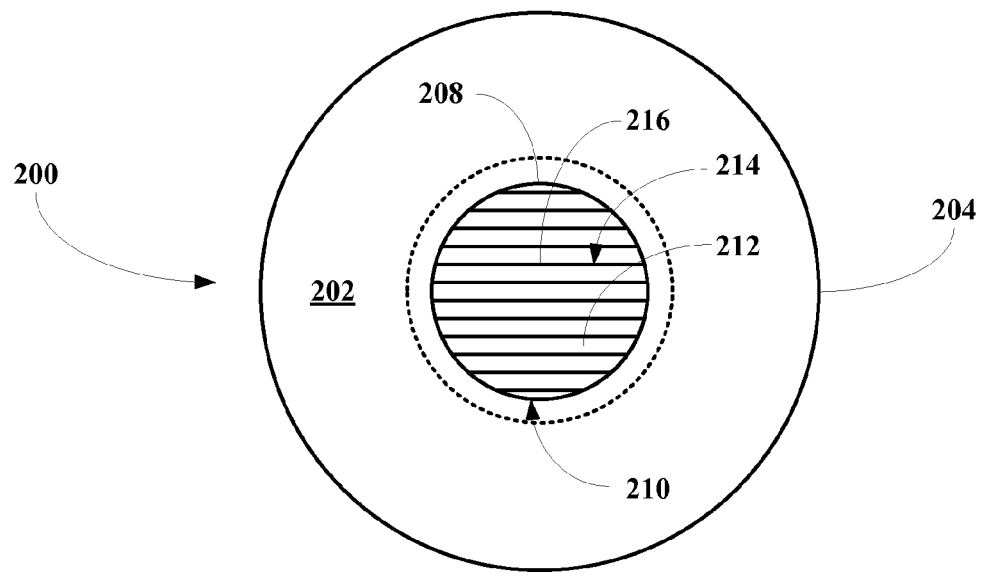

Referring now to FIGS. 2A&B, an embodiment of a secure barrel type container of this invention, generally 200, is shown to include a top 202, a cylindrical side 204, a bottom 205 and an interior 206. The top 202 includes a circular opening 208 having an embodiment of a second type of a unidirectional apparatus 210. The apparatus 210 includes a circular member 212 having a plurality of horizontal slits 214. The slits 214 and the resiliency of the material comprising the member 212 resist a user putting a hand or portion thereof into the opening 208 through the apparatus 210 and then attempting to remove material inside without suffering contact with edges 216 formed by the slits 214.

Referring now to FIGS. 3A-C, an embodiment of a secure box type container of this invention, generally 300, is shown to include a top 302, five side 304 (two of which are shown here) and an interior 306. The top 302 includes a slidable type of a unidirectional apparatus 308 and a circular opening 310. The apparatus 308 includes a hollow rectangular housing 312 having a circular housing opening 314. The housing 312 includes a inner slidable member 316 including a hollow cylinder 318 may optionally having a handle 320. The handle 320 is slidable within a longitudinal slot 322 in a side 324 of the housing 312. The slidable member 316 also included a tongue 326. The tongue 326 slides within a slot 328 in the top 302 of the container 300. Using the handle 320, the user moves the inner slidable member 316 until the hollow cylinder 318 aligns with the circular housing opening 314. The user then deposits material into the cylinder 318. Once the user deposits the material in the cylinder 318, using the handle 320, the user moves the inner slidable member 316 until the hollow cylinder 318 aligns with the circular opening 310. When the cylinder 316 is aligned with the opening 310, the material fall out of the cylinder 318 through the opening 310 and into the interior 306 of the container 300.

Figure 4A:
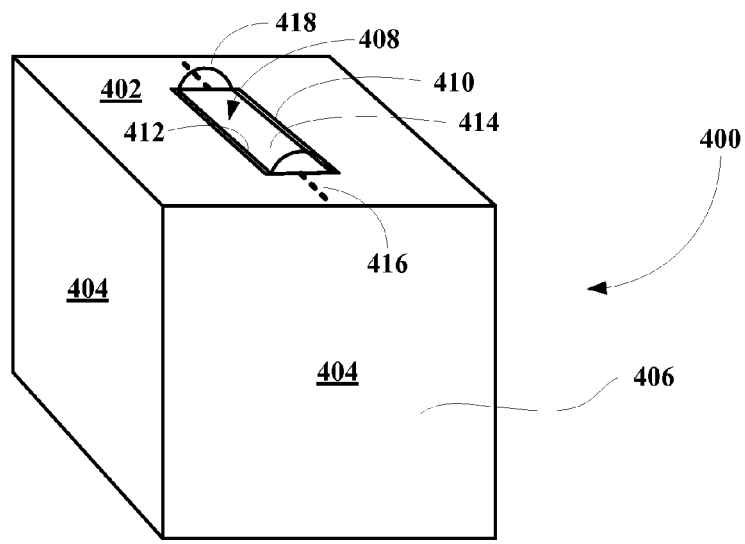
FIGS. 4A-B depict an embodiment of a secure box type container of this invention including a fourth type of unidirectional apparatuses of this invention.
Figure 4B:
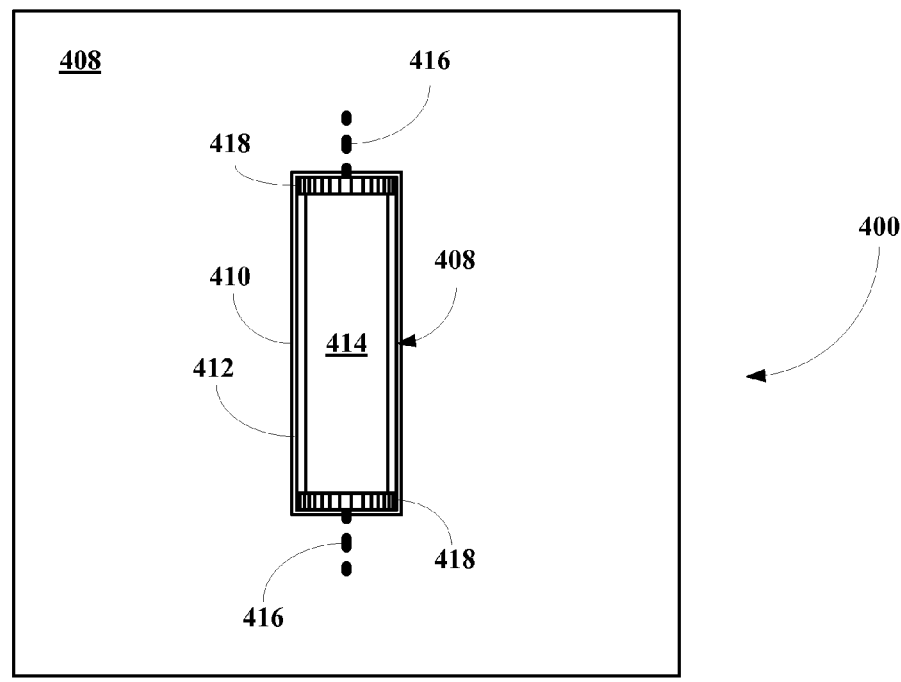

Referring now to FIGS. 4A&B, an embodiment of a secure box type container of this invention, generally 400, is shown to include a top 402, five side 404 (two of which are shown here) and an interior 406. The top 402 includes a rotatable type of a unidirectional apparatus 408 mounted in a rectangular opening 410. The apparatus 408 includes a hollow cylinder 412 having a slot 414 and mounted in the top 402 on shafts 416. The cylinder 410 also includes toothed ends 418 so that the cylinder may be rotated about the shafts 416. A user places material in the cylinder 412 via the slot 414. The user then rotates the cylinder 412 via the toothed ends 418 (one or both). When the cylinder 412 has rotated by 180°, the material fall out of the cylinder 412 through the slot 414 and into the interior 406 of the container 400.

Figure 4C:
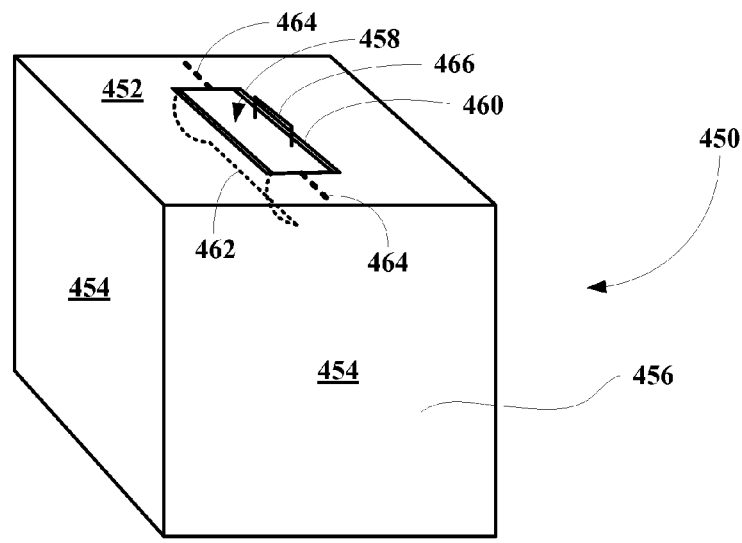
FIGS. 4C-D depict another embodiment of a secure box type container of this invention including a fourth type of unidirectional apparatuses of this invention.
Figure 4D:
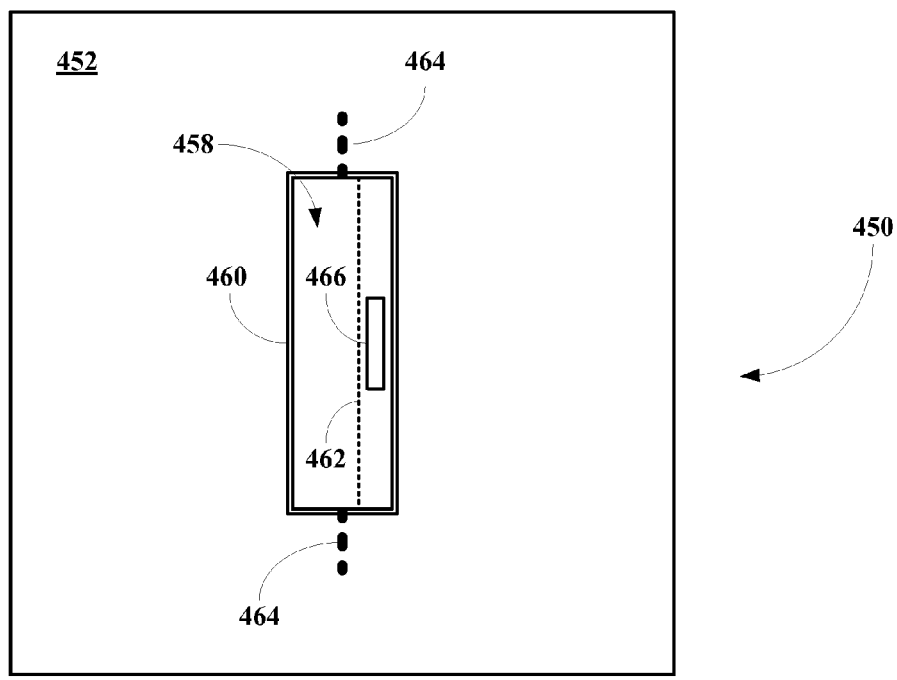

Referring now to FIGS. 4C&D, another embodiment of a secure box type container of this invention, generally 450, is shown to include a top 452, five side 454 (two of which are shown here) and an interior 456. The top 452 includes a rotatable type of a unidirectional apparatus 458 mounted in a rectangular opening 460. The apparatus 458 includes a hollow cylindrical scoop 462 mounted in the top 452 on shafts 464 shown in it closed position. The apparatus 458 also includes a handle 466 so that the scoop 462 may be rotated about the shafts 464. A user pulls the handle 466 to the left which rotates the scoop 462 to its opened position. Once the scoop 462 is in its opened position, the user places material in the scoop 462. The user then rotates the scoop 462 via the handle 466 back to its closed state depositing the material into the interior 456 of the container 450. This type of unidirectional apparatus is similar to the depositing apparatus used with mailboxes or bank night deposits.

Figure 5A:
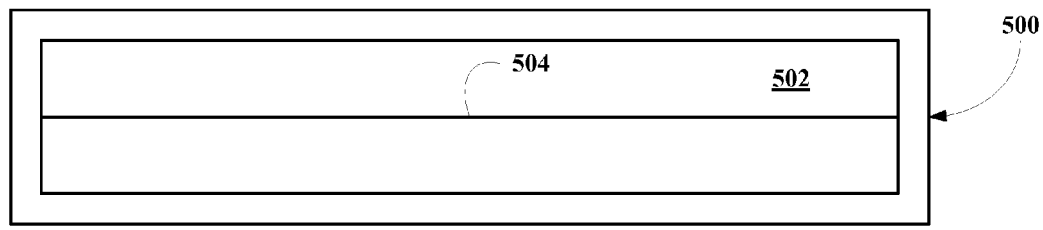
FIGS. 5A-H depict embodiments of the second type of unidirectional apparatuses of this invention.
Figure 5B:
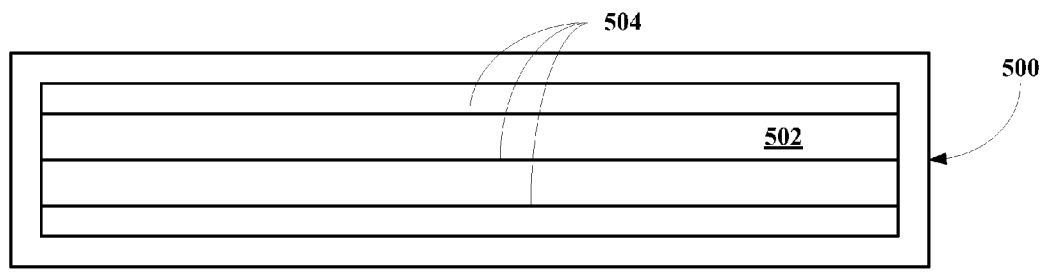
Figure 5C:
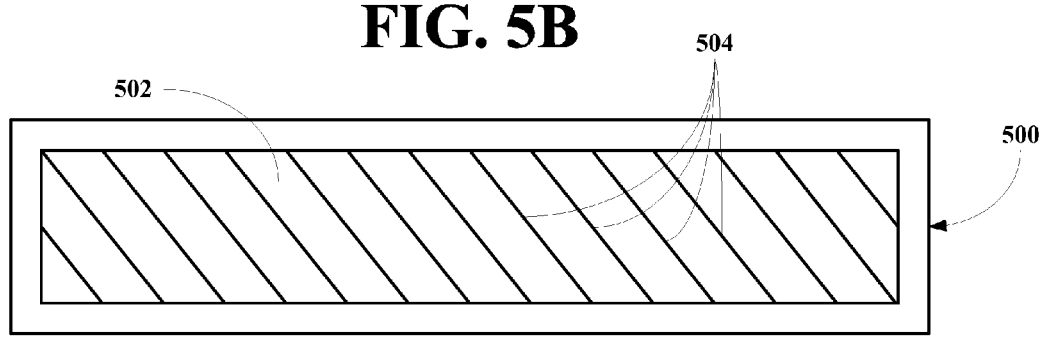
Figure 5D:
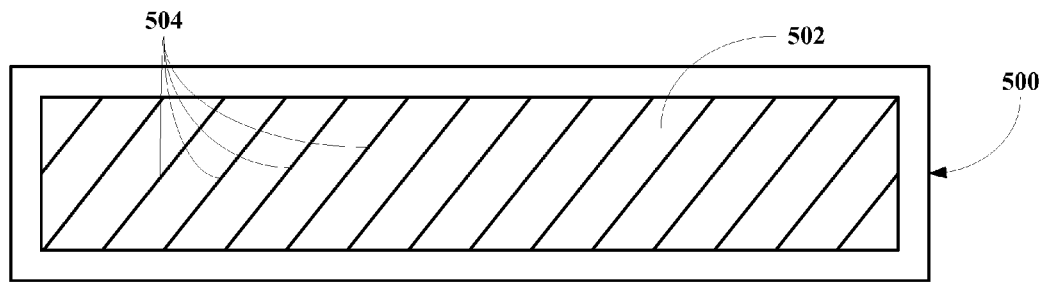
Figure 5E:
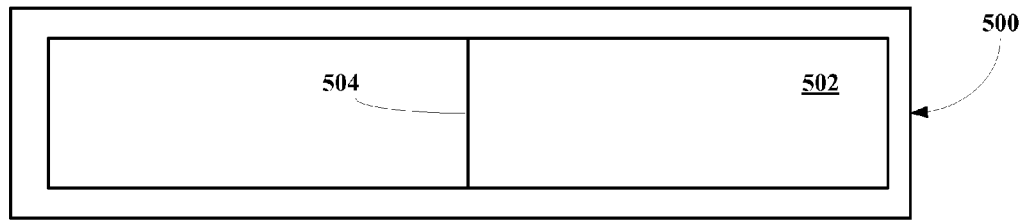
Figure 5F:
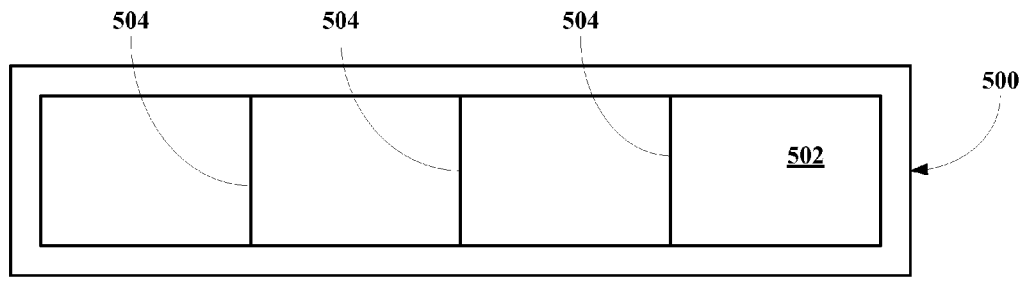
Figure 5G:
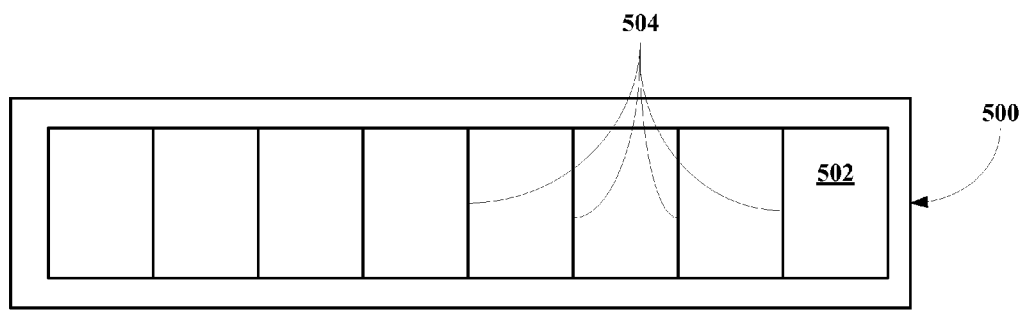
Figure 5H:
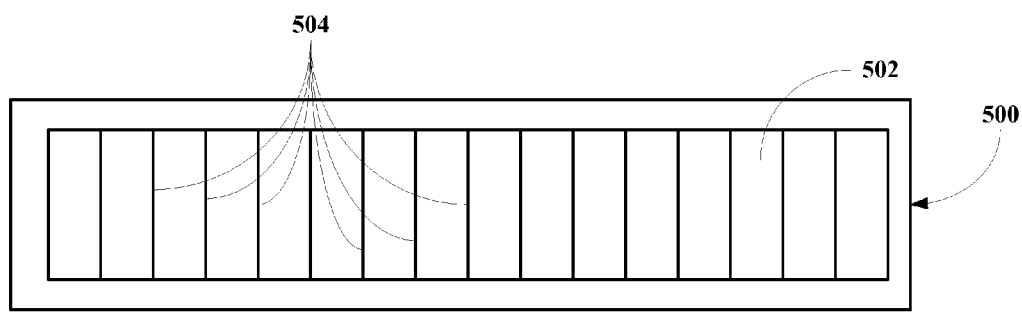

Referring now to FIG. 5A, an embodiment of a rectangular second type unidirectional apparatus, generally 500, is shown to include a rectangular member 502 having one longitudinal slit 504. Referring now to FIG. 5B, an embodiment of a rectangular second type unidirectional apparatus, generally 500, is shown to include a rectangular member 502 having a plurality of longitudinal slits 504. Referring now to FIG. 5C, an embodiment of a rectangular second type unidirectional apparatus, generally 500, is shown to include a rectangular member 502 having a plurality of left slanted slits 504. Referring now to FIG. 5D, an embodiment of a rectangular second type unidirectional apparatus, generally 500, is shown to include a rectangular member 502 having a plurality of right slanted slits 504. Referring now to FIG. 5E, an embodiment of a rectangular second type unidirectional apparatus, generally 500, is shown to include a rectangular member 502 having one lateral slit 504. Referring now to FIG. 5F, an embodiment of a rectangular second type unidirectional apparatus, generally 500, is shown to include a rectangular member 502 having three lateral slits 504. Referring now to FIG. 5G, an embodiment of a rectangular second type unidirectional apparatus, generally 500, is shown to include a rectangular member 502 having seven lateral slits 504. Referring now to FIG. 5H, an embodiment of a rectangular second type unidirectional apparatus, generally 500, is shown to include a rectangular member 502 having a plurality of lateral slits 504.

Referring now to FIG. 6A, an embodiment of a circular second type unidirectional apparatus, generally 600, is shown to include a circular member 602 having a plurality of vertical slits 604. Referring now to FIG. 6B, an embodiment of a circular second type unidirectional apparatus, generally 600, is shown to include a circular member 602 having a plurality of horizontal slits 606. Referring now to FIG. 6C, an embodiment of a circular second type unidirectional apparatus, generally 600, is shown to include a circular member 602 having a plurality of slanted slits 608.

Referring now to FIG. 7A, an embodiment of an ellipsoidal second type unidirectional apparatus, generally 700, is shown to include a circular member 702 having a plurality of vertical slits 704. Referring now to FIG. 7B, an embodiment of an ellipsoidal second type unidirectional apparatus, generally 700, is shown to include a circular member 702 having a plurality of horizontal slits 706.

Figure 8:
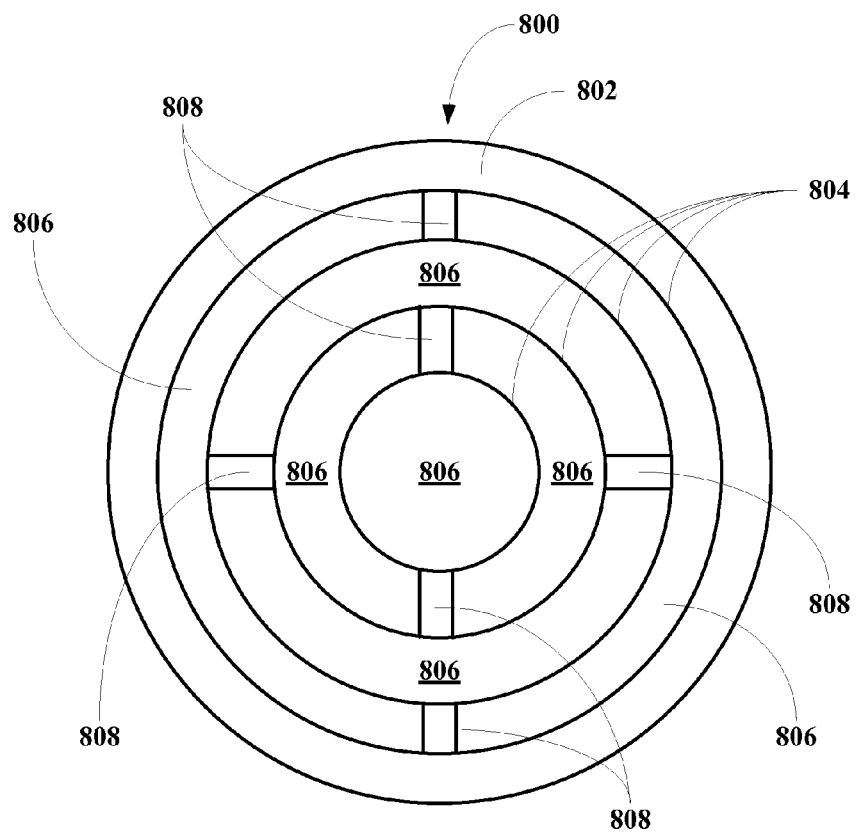
FIG. 8 depicts an embodiment of a fifth type of unidirectional apparatuses of this invention.
Figure 10A:
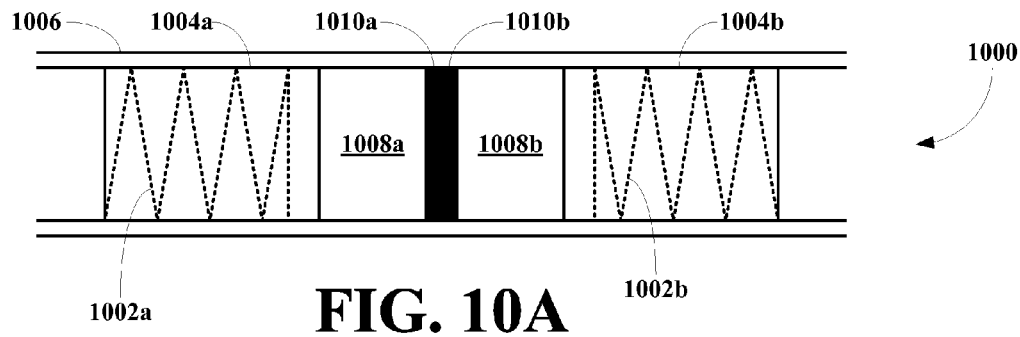
FIGS. 10A-D depicts another embodiment of a sixth type of unidirectional apparatuses of this invention.
Figure 10B:
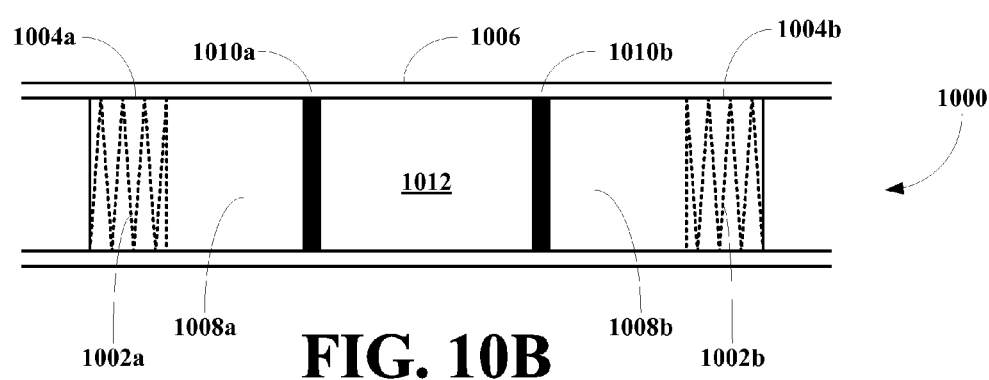
Figure 10C:
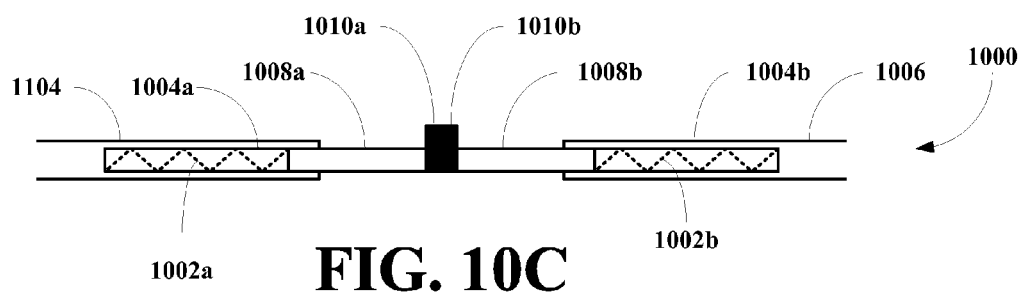
Figure 10D:
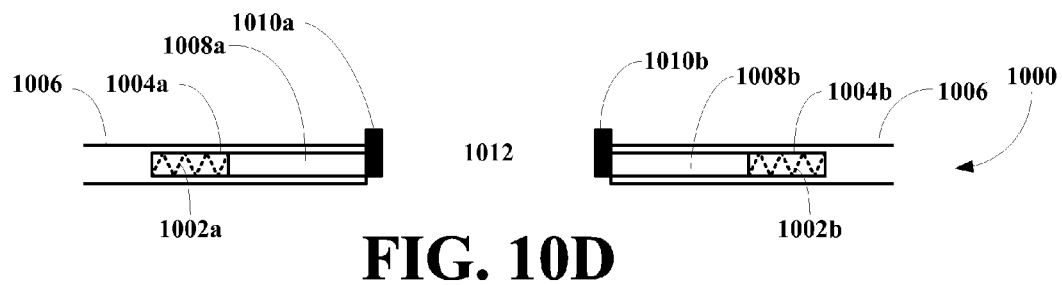

Referring now to FIG. 8, an embodiment of a circular fifth type unidirectional apparatus, generally 800, is shown to include a circular member 802 having a plurality of arcuate slits 804 and a plurality of arcuate or circular portions 806 that twist about tab portions 808. This same structure can be constructed using a rectangular member, an ellipsoidal member or any other geometrically shaped member.

Referring now to FIG. 9A-D, an embodiment of a biased unidirectional apparatus, generally 900, is shown to include a biased member 902 situated in a slot 904 in a top 906 of the container. The apparatus 900 also includes a movable member 908 having a upward extending member or handle 910 also disposed in the slot 904. Looking at FIGS. 9A&C, the apparatus 900 is shown in a closed state, where the biased member 902 is in a relaxed state. Looking at FIGS. 9B&D, the apparatus 900 is shown in an opened state, where the biased member 902 is in a compressed state. In the opened state, the apparatus 900 produces an opening 912 through which material can be deposited into the container. The biased member 902 provides a force to keep the opening 912 closed, until a person moves the movable member 908 to compress the bias member 902.

Referring now to FIGS. 10A-D, an embodiment of a biased unidirectional apparatus, generally 1000, is shown to include two biased members 1002*a*&*b* situated in slots 1004*a*&*b* in a top 1006 of a container (not shown). The apparatus 1000 also includes movable members 1008*a*&*b* having upward extending member or handles 1010*a*&*b* also disposed in the slots 1004*a*&*b*. Looking at FIGS. 10A&C, the apparatus 1000 is shown in its closed state, where the biased members 1002*a*&*b* are in their relaxed states. Looking at FIGS. 10B&D, the apparatus 1000 is shown in its opened state, where the biased members 1002*a*&*b* are in their compressed states. In its opened state, the apparatus 1000 produces an opening 1012 through which material can be deposited into the container. The biased members 1002*a*&*b* provides a force to keep the opening 1012 closed, until a person moves the movable members 1008*a*&*b* to compress the bias member 1002*a*&*b*.

Figure 11A:
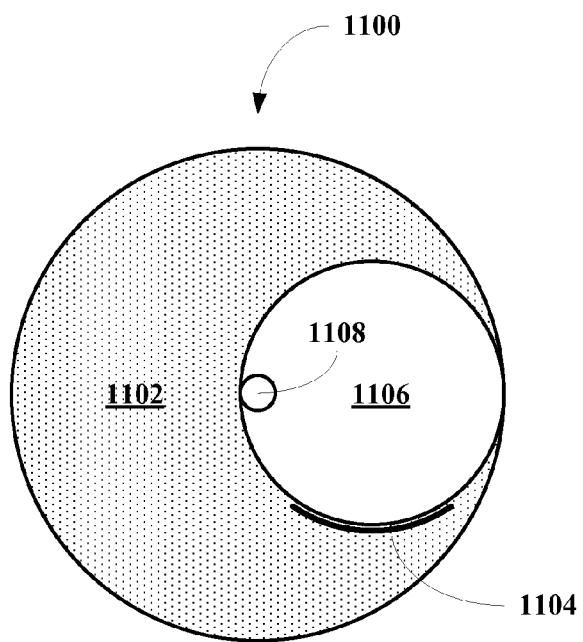
FIGS. 11A&B depicts another embodiment of a sixth type of unidirectional apparatuses of this invention.
Figure 11B:
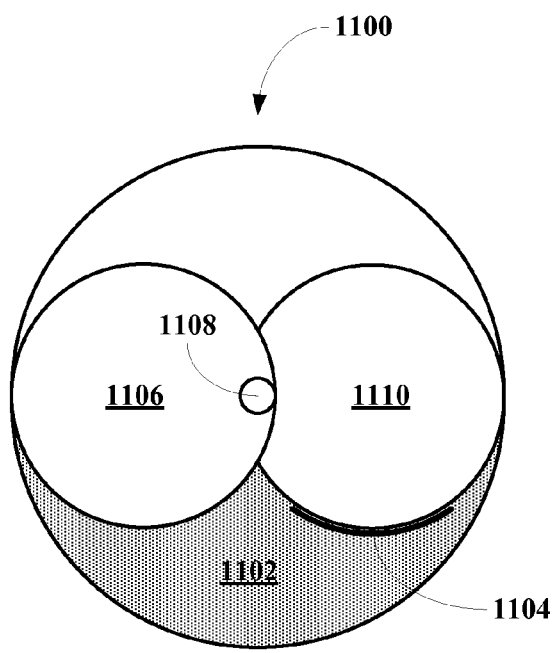

Referring now to FIGS. 11A&B, an embodiment of a circular biased unidirectional apparatus, generally 1100, is shown to include a biased member 1102, a stop 1104 and a circular member 1106 having a handle 1108. Looking at FIG. 11A, the apparatus 1100 is shown in a closed state, where the bias member 1102 is in a relaxed state. Looking at FIG. 11B, the apparatus 1100 is shown in an opened state, where the bias member 1102 is in a compressed state. In the opened state, the apparatus 1100 produces an opening 1110. The stop 1104 stops the circular member 1106 when the user lets go of the handle 1108 and the bias member 1102 forces the circular member 1106 back to the closed state.

Figure 12G:
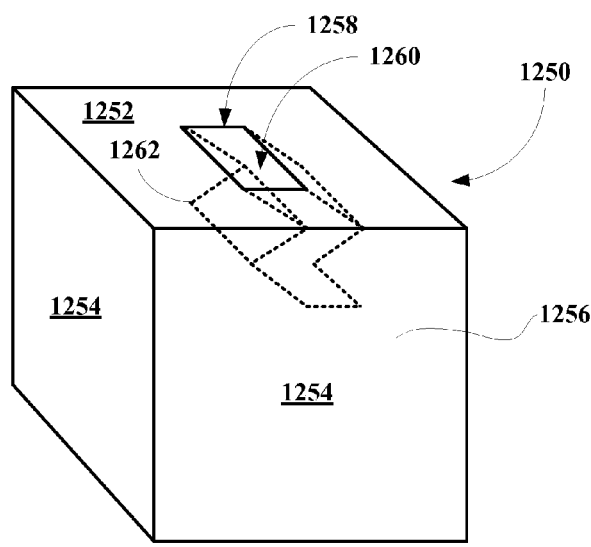
FIG. 12G-J, depict another embodiment of a seventh type of unidirectional apparatuses of this invention.
Figure 12I:
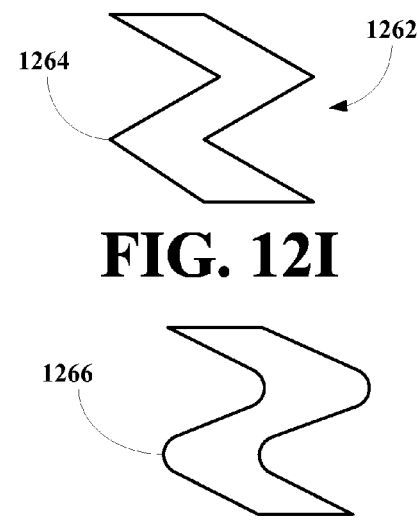
Figure 12J:
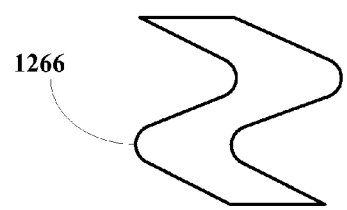
Figure 12H:
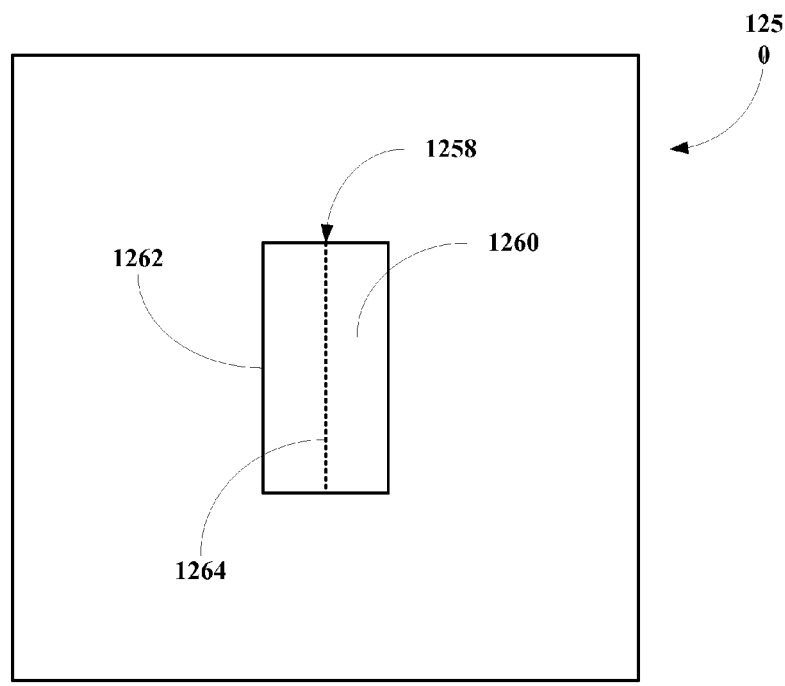

Referring now to FIGS. 12A-C, another embodiment of a secure box type container of this invention, generally 1200, is shown to include a top 1202, five side 1204 (two of which are shown here) and an interior 1206. The top 1202 includes a chute type of a unidirectional apparatus 1208 mounted in a rectangular opening 1210 in the container 1200. The apparatus 1208 includes a plurality of baffles 1212 extending in a downward inclination mounted on opposite walls 1214*a*&*b* so that the baffles alternate down a length of the chute. Looking at FIG. 12C, the apparatus 1208 is shown in a side view with the baffles 1212 alternating down the chute 1208 inclined at an angle $\alpha$ with respect to the walls 1214*a*&*b*. The user drops the material into the opening 1210 and the material is directed into the interior 1206 of the container by the baffles 1212, which resist normal attempts at removing materials from the container because the chute 1208 is baffled.

Referring now to FIGS. 12D-F, another embodiment of a secure box type container of this invention, generally 1230, is shown to include a top 1232, five side 1234 (two of which are shown here) and an interior 1236. The top 1232 includes a chute type of a unidirectional apparatus 1238 mounted in a circular opening 1240 in the container 1230. The chute 1238 has a spiral configuration, where the chute defines a spiral path for materials dropped into the opening. The user drops the material into the opening 1240 and it follows the spiral pathway into the interior 1236 of the container by the spiraled chute 1238, which is configured to resist normal attempts at removing materials from the container. The spiral chute 1238 may be opened as shown here or closed—a spiraled length of rectangular, circular or any other cross-sectional shaped tubing. The opening 1240 may be of any desired shape.

Referring now to FIGS. 12G-J, another embodiment of a secure box type container of this invention, generally 1250, is shown to include a top 1252, five side 1254 (two of which are shown here) and an interior 1256. The top 1252 includes a chute type of a unidirectional apparatus 1258 mounted in a rectangular opening 1260 in the container 1250. The chute 1258 comprises a closed zig-zag shaped conduit 1262. The conduit 1262 defines a zig-zag path into the interior 1256 of the container 1250. The user drops the material into the opening 1260 and it follows the zig-zag pathway into the entire 1256 of the container by the zig-zag chute 1258, which is configured to resist normal attempts at removing materials from the container. Looking at FIGS. 12I&J, cross-sectional views of two embodiments of the conduits of this unidirectional apparatus 1258 are shown. The conduit of FIG. 12I has sharp corners 1264, while the conduit of FIG. 12J has rounded corners 1266.

Figure 13:
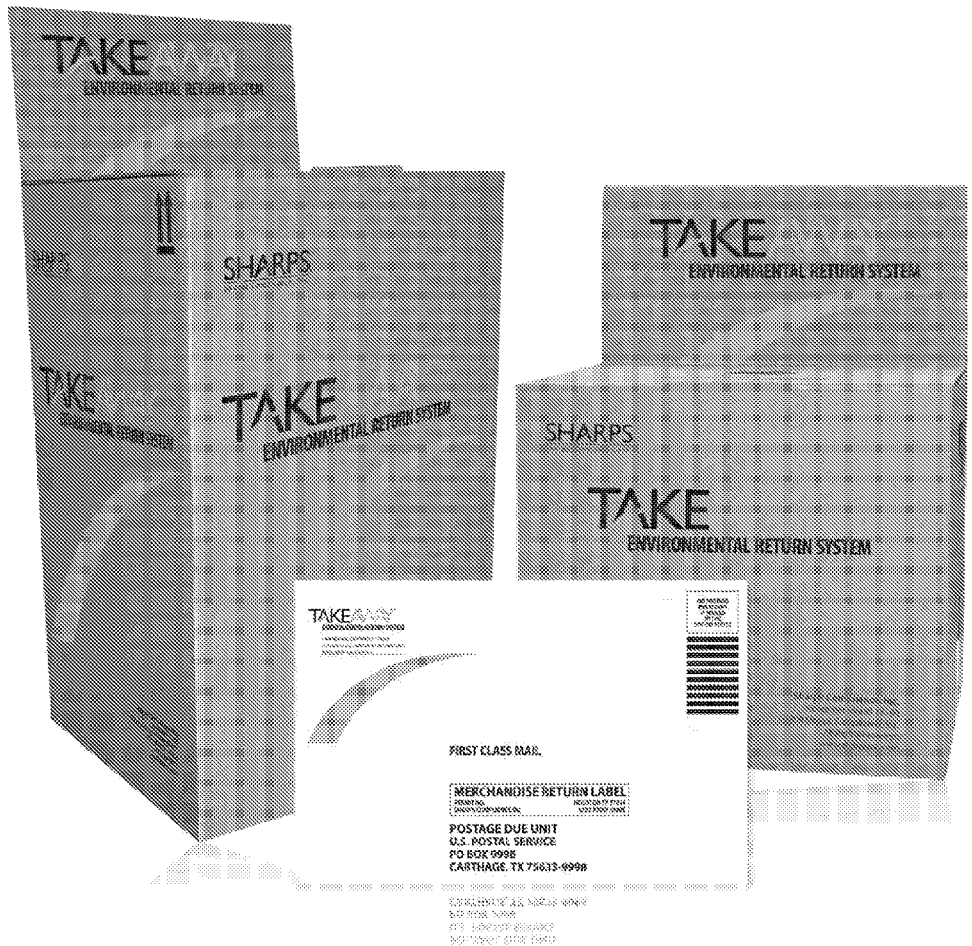
FIG. 13 depicts a photograph of embodiments of the invention.

Referring now to FIG. 13, photographs of embodiments of containers of this invention are shown, where the containers includes a first type unidirectional apparatus and a second type unidirectional apparatus and a sealing member.

All references cited herein are incorporated by reference to the full extent as permitted by 35 U.S.C. et seq., 37 CRF et seq. and the MPEP et seq. Although the invention has been disclosed with reference to its preferred embodiments, from reading the present description, those of skill in the art may appreciate changes and modification that may be made which do not depart from the scope and spirit of the invention as described above and claimed hereafter.

We claim:

1. A method comprising:
   positioning a secure container at a location where source materials are generated, where the container comprises:
   a body including:
   at least one sidewall,
   a bottom, and
   a top having at least one opening including a unidirectional apparatus,
   an interior defined the top, the at least one sidewall, and the bottom,
   where the unidirectional apparatus permits source material to be deposited into the interior of the container, while resisting normal attempts of retrieval of the source material deposited therein,
   placing the source materials into an interior of a container through an opening in the container to fill the container,
   sealing a filled container and/or sealing the openings of the filled container to form a sealed container,
   transporting the sealed container via a delivery service to a processing facility.

2. The method of claim 1, wherein the unidirectional apparatus comprises a first type unidirectional apparatus, a second type unidirectional apparatus, a third type unidirectional apparatus, a fourth type unidirectional apparatus, a fifth type unidirectional apparatus a sixth type unidirectional apparatus, a seventh type unidirectional apparatus or mixtures and combinations thereof.

3. The method of claim 2, wherein the first type unidirectional apparatus comprises a member having a plurality of radial slits so that a source material can be pushed through the slits.

4. The method of claim 3, wherein the member is a flat or substantially flat.

5. The apparatus of claim 3, wherein the member comprises a regular shape or an irregular shape and the radial slits extend from a center of the member outward to a boundary for affixing the member into the top of the container.

6. The method of claim 2, wherein the second type unidirectional apparatus comprises member having one longitudinal, lateral, or slanted slit or a plurality of such slits.

7. The method of claim 6, wherein the member is a flat or substantially flat.

8. The method of claim 6, wherein the member comprises a regular shape or an irregular shape and the radial slits extend from a center of the member outward to a boundary for affixing the member into the top of the container.

9. The apparatus of claim 6, wherein the plurality of slits are arranged in a pattern.

10. The method of claim 2, wherein the third type unidirectional apparatus comprises a housing having an opening in its top and a slidable member disposed in an interior of the housing, the slidable member includes a hollow cavity into which a source material is be placed, the slidable member is slidable within the housing and movable within a longitudinal slot in the housing, once a source material is placed in the hollow cavity, the slidable member is moved so that the hollow member aligns with an opening in the top of the container so that the material falls into an interior of the container.

11. The method of claim 2, wherein the fourth type of unidirectional apparatuses include a rotatable member having an opened interior, where rotation of the member through an angle of 180° resulting in material placed the opened interior being deposited in the interior of the container.

12. The method of claim 2, wherein the fifth type unidirectional apparatus comprises member having one or a plurality of arcuate slits and tabs, where the arcuate slits form portions of member that rotate about the tabs allowing material to pass into the interior of the container.

13. The method of claim 12, wherein the member is a flat or substantially flat.

14. The method of claim 1, wherein the sixth type unidirectional apparatus comprises at least one biased slidable member including a handle mounted in an opening in the top of the container, when the slidable member is moved to open the opening, the biased member is compressed, once material is placed into the container through the opening, the slidable member is released and the biased member quickly restores the slidable member to its closed state.

15. The method of claim 1, wherein the seventh type unidirectional apparatus comprises at least one chute, where the chute include a plurality of baffles or defines a spiral or zig-zag path.

16. The method of claim 1, further comprising:
    post-processing the sealed container to alter or change specific combustion properties of the filled container or to impart designed barrier properties to the filled container.

17. The method of claim 16, wherein the barrier property includes gas resistance, water resistance, solvent resistance, hardening, and/or other barrier properties to the filled container.

18. The method of claim 1, further comprising:
    burning the sealed containers and/or the post-processed sealed container in a combustion facility, where either a portion of generated heat from combustion of the containers is converted into a useable form of energy or a portion of the generated heat and the ash is used to form a useable product.

* * * * *